United States Patent [19]

Kiyoto et al.

[11] Patent Number: 4,680,178
[45] Date of Patent: Jul. 14, 1987

[54] ANTITUMOR AGENT COMPRISING FR-900216

[75] Inventors: Sumio Kiyoto, Ikeda; Masakuni Okuhara, Sakura; Eiko Kino, Tsuchiura; Hirokazu Tanaka, Sakura; Hatsuo Aoki, Ikeda; Masanobu Kohsaka, Sakai; Hiroshi Imanaka, Osaka, all of Japan

[73] Assignee: Fujisawa Pharmaceutical Co., Ltd., Osaka, Japan

[21] Appl. No.: 631,244

[22] Filed: Jul. 16, 1984

[30] Foreign Application Priority Data

Jul. 21, 1983 [JP] Japan ............................. 58-133506
Mar. 2, 1984 [JP] Japan ............................. 59-40748

[51] Int. Cl.$^4$ .................... A61K 35/70; A61K 35/72; A61K 31/42

[52] U.S. Cl. ................................ 424/122; 514/374
[58] Field of Search ............... 548/235; 424/272, 122; 514/374

[56] References Cited

PUBLICATIONS

Carter, S. K., M.D. et al, "Chemotherapy of Cancer", pp. 26–43, 2 ed. John Wiley & Sons, N.Y.
Iwasaki, S. et al., Chem. Abst. 101:5132c (1984).

*Primary Examiner*—Jerome D. Goldberg
*Attorney, Agent, or Firm*—Oblon, Fisher, Spivak, McClelland & Maier

[57] ABSTRACT

The invention relates to a pharmaceutical composition for treating lymphocytic leukemia, melanoma or mammary carcinoma comprising an effective amount of FR-900216.

2 Claims, 1 Drawing Figure

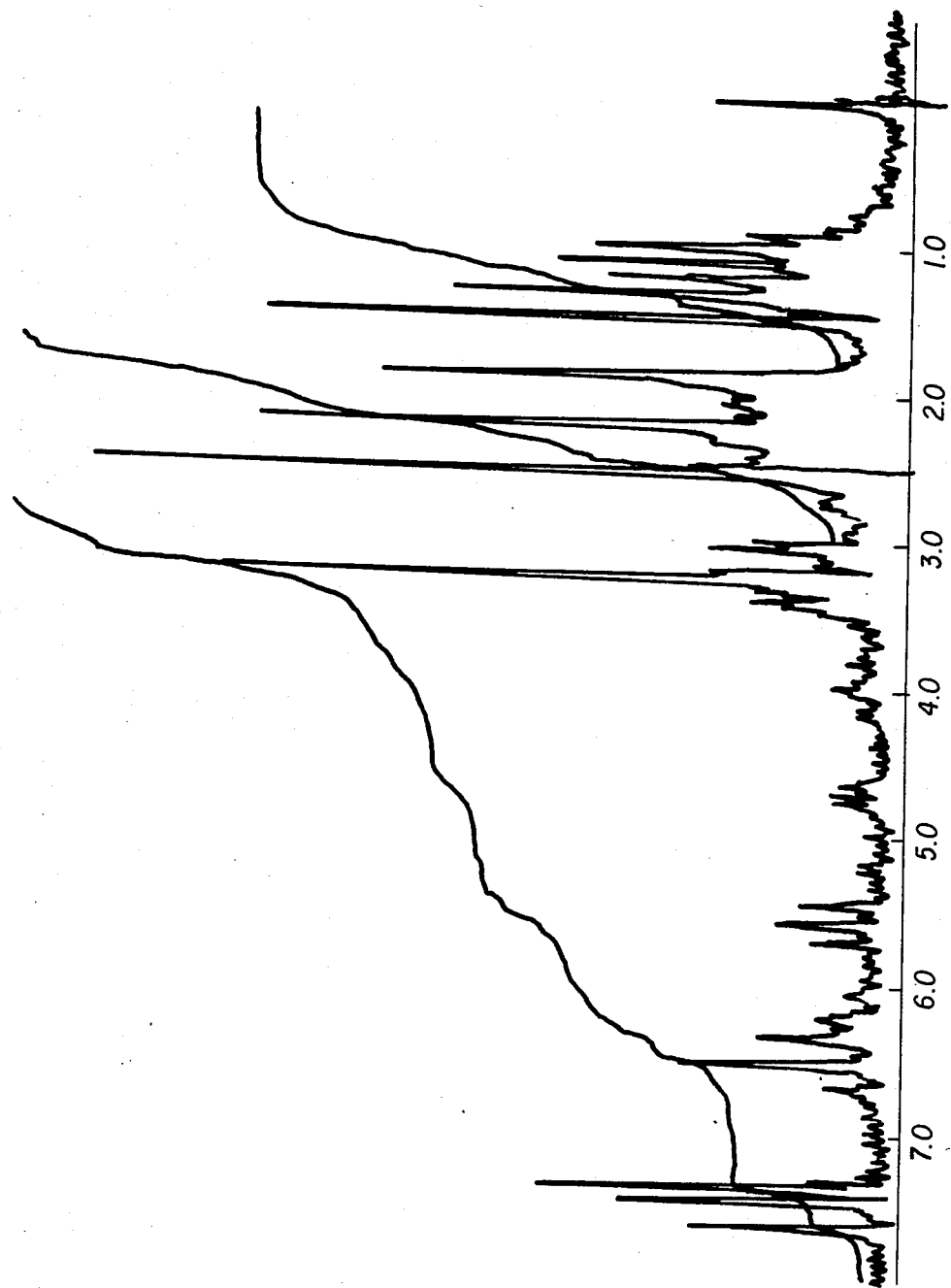

ANTITUMOR AGENT COMPRISING FR-900216

This invention relates to an agent containing FR-900216 substance or its pharmaceutically acceptable salts as an active ingredient for treatment of lymphocytic leukemia, melanoma or mammary carcinoma in a subject.

FR-900216 substance has the following physical and chemical properties:
(1) Molecular weight:
  625 (Mass spectrum)
(2) Molecular formula:

$C_{35}H_{47}NO_9$ (3) Melting point:
  130°–135° C. (dec.)
(4) Specific rotation:
  $[\alpha]_D^{20} = +140°$ C. (c=1, CHCl$_3$)
(5) Ultraviolet absorption spectrum:

$\lambda_{max}^{CH3OH}$ = 232 nm ($\epsilon$ = 11,300)

= 238 nm (sh.)

= 285 nm (sh.)

= 296 nm ($\epsilon$ = 55500)

= 308 nm ($\epsilon$ = 70300)

= 324 nm ($\epsilon$ = 51900)

(6) Infrared absorption spectrum:
  $\nu_{max}^{KBr}$: 3450, 3140, 2960, 2920, 2860, 1730, 1715 (sh.), 1607, 1575, 1455, 1445, 1435, 1377, 1360, 1343, 1305, 1280, 1260, 1225, 1190, 1170, 1140, 1107, 1077, 1045, 1030 (sh.), 980, 970, 950, 930, 915, 905, 895, 875, 860, 850, 835, 825, 790, 780, 755, 705, 670, 635 cm$^{-1}$
(7) $^1$H Nuclear magnetic resonance spectrum (CDCl$_3$, inner standard: tetramethylsilane):
  It is shown in FIGURE of the accompanying drawing.
(8) $^{13}$C Nuclear magnetic resonance spectrum (CDCl$_3$, inner standard: tetramethylsilane):
  δ (ppm): 9.65, 11.41, 11.71, 13.77, 14.32, 16.93, 22.57, 29.24, 31.49, 31.85, 34.16, 35.86, 36.40, 37.98, 45.32, 54.18, 56.12, 63.77, 65.10, 76.81, 82.33, 89.25, 120.80, 123.77, 126.44, 129.29, 135.97, 136.21, 136.57, 137.67, 138.51, 139.54, 160.84, 168.01, 169.34
(9) Solubility:
  Freely soluble: methanol, ethanol, acetone, ethyl acetate
  Soluble: chloroform, benzene
  Slightly soluble: hexane, diethyl ether
  Insoluble: water
(10) Color reaction:
  Positive: Dragendorff's reaction, iodine reaction
  Negative: Ferric chloride reaction, Molisch's reaction, Ninhydrin reaction, Ehrlich's reaction
(11) Nature:
  Weekly basic substance The FR-900216 substance, active ingredient of this invention, is presumed to be the same compound to "Rhizoxin" which was published in the Symposium Papers of the 25th Symposium on the Chemistry of Natural Products held in Tokyo in 1982.

Said "Rhizoxin" has a following structural formula:

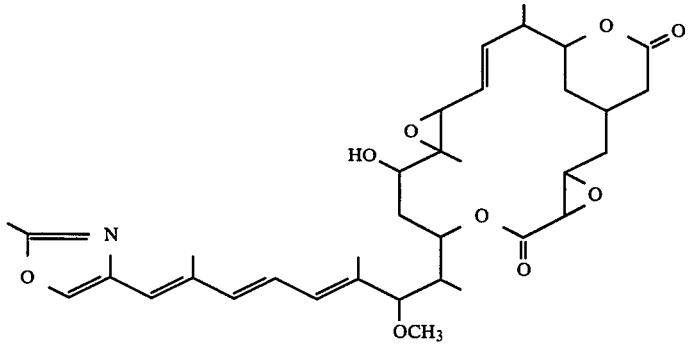

FR-900216 substance can be produced by fermentation of FR-900216 substance-producing strain belonging to the to the genus Rhizopus such as Rhizopus sp. No. F-1360 or the like in a nutrient medium.

Particulars of microorganism used for producing FR-900216 substance and production thereof will be explained in the following.

The microorganism which can be used for the production of FR-900216 substance is a strain belonging to the genus Rhizopus, among which a strain of Rhizopus sp. No. F-1360 has been newly isolated from a soil sample collected at Uji-shi, Kyoto-fu, Japan.

Taxonomic characteristics of Rhizopus sp. No. F-1360:
(1) Morphological characteristics:
(a) Macroscopic observation:
  (i) Cultures on malt extract agar:
    Colonies spread broadly, attaining over 8.0 cm in diameter after 3 to 5 days at 30° C., and finally the Petri dish is covered with the myceria. The colony surface is plane and thick. While young cultures are white, they become gray or black with formation and maturation of sporangia and spores. The sporangia and spores are formed in abundance. The colony margin is cobweb-like, and aerial mycelia arise up to the walls of Petri dishes or slant tubes. The reverse is hyaline or pale yellow. Neither soluble pigments nor exudations are produced. The odor is sweet-smelling. It grows slowly at 25° C.
  (ii) Cultures on YpSs agar:
    Colonies are the same as on malt extract agar.
  (iii) Cultures on potato dextrose agar:
    They are the same as on malt extract agar.
  (iv) Cultures on Czapek's solution agar:
    They grow much restrictedly.
(b) Microscopic observation:
  The sporangia are covered with the thin-walled membrane. When they mature, they burst and discharge a number of enterogenous spore. They are globose and 30-200 μm in diameter. The sporangiospores are ellipsoidal, 7.5×15 μm in size, smooth to wrinkled. The substratal mycelia are non-septate, and they form the rhizoids. Each of the sporangiophores is connected by stolons and the columella is formed at the top of them.

(2) Physiological characteristics:

(a) Temperature range for growth:

This strain can grow at temperature in the range from 10° to 48° C. with the growth optimum at 33° C. And they can form sporangia from 14° to 39° C. These data were determined on potato dextrose agar.

(b) Growth in Pfeffer solution:

This strain can grow at temperature range from 25° to 42° C.; no growth at 10° C.

(c) pH range for growth:

This strain can grow at pH 2.5 to 12.0 on malt extract agar and YpSs agar.

(d) Production of organic acids:

This stain produce organic acids.

From above-mentioned characteristics, the stain was considered to be one strain of the zygomycete genus Rhizopus Ehrenb. Consequently, the strain was named to Rhizopus sp. No. F-1360.

A culture of Rhizopus sp. No. F-1360 has been deposited with ATCC (American Type Culture Collection, 12301 Parklawn Drive Rockville, Md. 20852, U.S.A.) on Nov. 21, 1979 under the number of ATCC 20577, and the deposit is now requested to be converted for Budapest Treaty purposes.

This invention also includes the use of any mutants which are capable of producing FR-900216 substance, including natural mutants which are produced by natural mutation of the organism as well as artificial mutants which can be produced from the described organism by conventional means, such as X-rays, ultraviolet radiation, treatment with a mutating agent such as nitrogen mustard oils, azaserine, nitrous acid, 2-aminopurine, N,N'-nitro-N-nitrosoguanidine (NTG) or the like, treatment with phage, transformation, transduction, conjugation and the like.

The FR-900216 substance of this invention is produced when a FR-900216 substance producing strain belonging to the genus Rhizopus (e.g. Rhizopus sp. No. F-1360 ATCC 20577) is grown in a nutrient medium containing sources of assimilable carbon and nitrogen under aerobic conditions (e.g. shaking culture, submerged culture, etc.).

The preferred sources of carbon in the nutrient medium are carbohydrates such as glucose, sucrose, maltose, glycerin, starch, soluble starch, dextrin and the like.

The preferred sources of nitrogen are meat extract, hydrolyzed casein, peptone, gluten meal, corn meal, cotton seed flour, soy bean meal, corn steep liquor, dried yeast, yeast extract, urea, ammonium phosphate, etc.

The carbon and nitrogen sources, though advantageously employed in combination, need not to be used in their pure form, because less pure materials which contain traces of growth factors and considerable quantities of mineral nutrients are also suitable for use.

When desired, there may be added to the medium mineral salts such as disodium or dipotassium hydrogen phosphate, magnesium chloride, magnesium sulfate, calcium carbonate and the like.

If necessary, especially when the culture medium foams seriously a defoaming agent, such as plant oil (soy bean oil, linseed oil, etc.), liquid paraffin, fatty oil, higher alcohol (octadecanol, tetradecanol, heptanol, etc.), silicone may be added.

Submerged aerobic cultural conditions are preferred for the production of FR-900216 substance in massive amounts. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of FR-900216 substance. Accordingly, it is desirable first to produce a vegetative inoculum of the organism by inoculating a relatively small quantity of culture medium with spores or mycelia of the organism and culturing said inoculated medium, and then to transfer the cultured vegetative inoculum aseptically to large tanks. The medrum, in which the vegetative inoculum is produced, is substantially the same as or different from the medium utilized for the production of the FR-900216 substance.

Agitation and aeration of the culture mixture may be accomplished in a variety of ways. Agitation may be provided by a propeller or similar mechanical agitation equipment, by revolving or shaking the fermentor, by varios pumping equipment or by the passage of sterile air through the medium. Agitation may be effected by passing sterile air through the fermentation mixture.

The fermentation is usually conducted at a temperature between about 20° C. and 40° C., preferably 25°–35° C., for a period of about 50 hours to 100 hours.

Thus produced FR-900216 substance can be recovered from the cultured medium by conventional means which are commonly used for the recovery of other known biologically active substances. The FR-900216 substance may be included in both of filtered broth and cultured myceria, but, in general, most of FR-900216 substance are found in the cultured myceria. FR-900216 substance can be extracted from the cultured myceria with a solvent such as ethyl acetate and the like. Further, FR-900216 substance can be isolated or purified from thus obtained extract or filtered broth by a conventional manner such as concentration under reduced pressure, extraction with solvent, treatment with resin (e.g. anion or cation exchange resin, non-ionic adsorption resin), treatment with a conventional adsorbent (e.g. activated charcol, silicic acid, silica gel, alumina cellulose, etc.), crystallization, recrystallization, column chromatography using silica gel and the like, liquid column chromatography using silica gel and the like, and the like.

Thus obtained FR-900216 substance can be converted to the corresponding pharmaceutically acceptable salt thereof by treating it with an acid by a conventional manner.

Suitable pharmaceutically acceptable salt of FR-900216 substance may include inorganic or organic acid addition salts such as acetic acid salt, lactic acid salt, maleic acid salt, fumaric acid salt, oxalic acid salt, citric acid salt, methanesulfonic acid salt, hydrochloric acid salt, sulfuric acid salt, phosphoric acid salt and the like.

The pharmaceutical composition of this invention can be used in the form of a pharmaceutical preparation, for example, in solid, semisolid or liquid form, which contains FR-900216 substance or its pharmaceutically acceptable salts, as an active ingredient in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions emulsions, suspensions, and any other form suitable for use. And, if necessary, in addition, auxiliary, stabilizing, thickening and coloring agents and perfumes may be used. FR-900216 substance is included in the pharmaceutical composition in an amount sufficient to produce the desired effect upon lymphocytic leukemia, melanoma or mammary carcinoma in a subject.

For applying this composition to the subject, it is preferably to apply it by intravenous, intramuscular or oral administration. While the dosage of therapeutically effective amount of FR-900216 substance varies from and also depends upon the age and condition of each individual subject to be treated, in the case of intravenous administration, a daily dose of 0.01–1 mg/kg, preferably about 1 mg/kg, in the case of intramuscular administration, a daily dose of 0.1–10 mg/kg, preferably about 1 mg/kg, in case of oral administration, a daily dose of 0.5–50 mg/kg, preferably about 5 mg/kg of FR-900216 substance is generally given for treating lymphocytic leukemia, melanoma or mammary carcinoma in a subject.

The activity of FR-900216 substance is explained in the following.

TEST 1

Activity of FR-900216 substance against Lymphocytic Leukemia L1210 and P388:

(1) Intraperitoneal administration:
Method

Lymphocytic Leukemia (L1210 or P388) cells were successively transferred to DBA/2 mice. On day 7, ascites was collected from the intraperitoneal cavity to isolate the tumor cells, from which the suspension of the tumor cells was prepared. The cell suspension (0.2 ml) containing $10^5$ cells (L1210) or $10^6$ cells(P388) was implanted intraperitoneally to female BDF$_1$ mice (7 weeks old and weighing 17.9 g to 21.7 g in the case of L1210, and 8 weeks old and weighing 18.4 to 22.5 g in the case of P388).

The sample of FR-900216 substance used in the experiment was solubilized in methanol, concentrated in vacuo and then suspended in the sterilized water.

After 24 hours of the implantation of the tumor cells to the mice, FR-900216 substance was administered intraperitoneally in the graded doses, respectively in each medicated group (water only in the control group) once a day for 4 days.

Antitumor activity of FR-900216 substance was evaluated by the increase in life-span of the medicated group over the control groups (T/C×100) in leukemias, wherein T is median survival time (MST) of the medicated group, and C is median survival time of the control group.

Result

The test result is shown in the following Table 1.

TABLE 1

| Tumor cells | Dosed/Control | No. of mice | Single dose (mcg/kg) | Toxic death | Mean survival time (days) | T/C × 100 (%) | Weight change (g) day 0 to day 4 |
|---|---|---|---|---|---|---|---|
| Lymphocytic Leukemia L1210 | dosed with FR-900216 substance | 10 | 1000 | 0 | 13.1 | 152 | −1.8 |
| | | 10 | 500 | 0 | 11.3 | 131 | −0.6 |
| | | 10 | 250 | 0 | 10.4 | 121 | −0.1 |
| | | 10 | 125 | 0 | 9.3 | 108 | +0.2 |
| | Control | 20 | — | 0 | 8.6 | 100 | +0.6 |
| Lymphocytic Leukemia P388 | dosed with FR-900216 substance | 10 | 500 | 0 | 14.5 | 121 | −2.7 |
| | | 10 | 250 | 0 | 16.0 | 133 | −2.2 |
| | | 10 | 125 | 0 | 14.0 | 117 | −1.7 |
| | Control | 20 | — | 0 | 12.0 | 100 | −1.0 |

(2) Oral administration:
Method

Lymphocytic Leukemia L1210 cells were successively transferred to DBA/2 mice. On day 7, ascites was collected from the intraperitoneal cavity to isolate the tumor cells, from which the suspension of the tumor cells was prepared. The cell suspension (0.2 ml) containing $10^5$ cells was implanted intrapertoneally to BDF$_1$ mice 7 weeks old and weighing 17.9 to 21.7 g.

The sample of FR-900216 substances used in the experiment was solubilized in methanol, concentrated in vacuo and then suspended in the sterilized water.

After 24 hours of the implementation of the tumor cells to the mice, FR-900216 substance was administered orally in the doses of 10,000 and 30,000 mcg/kg, respectively in each medicated group (water only in th control group) once a day for 4 days.

Antitumor activity of FR-900216 substance was evaluated by the increase in life-span of the medicated group over the control group (T/C×100) in leukemia, group, and C is the median survival time of the control group.

Result

The test result is shown in the following Table 2.

TABLE 2

| Tumor cells | Dosed/Control | No. of mice | Single dose (mcg/kg) | T/C × (%) |
|---|---|---|---|---|
| Lymphocytic Leukemia L1210 | dosed with FR-900216 substance | 5 | 30000 | 173 |
| | | 5 | 10000 | 122 |
| | Control | 5 | — | 100 |

TEST 2

Activity of FR-900216 substance against Melanoma B16:
Method

On 14 days after subcutaneous implantation of Melanoma B16 cells to DBA/2 mouse, one gram of the tumor was aseptically separated from mouse and homogenized in 10 ml of Hank's solution. 0.5 ml of the homogenate was inoculated to BDF$_1$ mouse weighing 19.7 to 28.4 g of 12 weeks age. Twenty-four hours after the implantation of the tumor cells, graded doses of FR-900216 substance was administered to mice intraperitoneally once a day on day 1, 2, 3 and 4. FR-900216 substance was first dissolved into methanol, concentrated in vacuo by adding water and finally obtained in aqueous suspension. A tumor activity was evaluated by T/C (%) as described in Test 1.

Result

The test result is shown in the following Table 3.

TABLE 3

| Tumor cells | Dosed/Control | No. of mice | Single dose (mcg/kg) | Toxic death | Mean Survival time (days) | T/C × 100 (%) | Weight change (g) day 0 to day 4 |
|---|---|---|---|---|---|---|---|
| Mouse melanoma B16 | dosed with FR-900216 substance | 10 | 1000 | 0 | 19.0 | 136 | −3.6 |
| | | 10 | 500 | 0 | 17.5 | 125 | −0.6 |
| | | 10 | 250 | 0 | 17.0 | 121 | +0.2 |
| | Control | 20 | — | 0 | 14.0 | 100 | −0.2 |

TEST 3

Activity of FR-900216 substance for subrenal capsule human mammary carcinoma MX-1 xenograft:

Method

The antitumor activity of FR-900216 substance was determined in experimental tumor system in Swiss-nu/nu mice. Swiss-nu/nu mice were subcutaneously implanted with a 2×2×2 mm fragment of MX-1 cells. When donor tumor reached approximately 1 g (30 days after the implantation of tumor cells), MX-1 cells were implanted with a 1×1×1 mm$^3$ fragment under the subrenal capsule, using a 16 gauge trocar after exposing the kidney with a 7 mm dorsal skin incision. The wound was closed with a 9 mm wound clip after closing the peritoneum with 1-4 silk sutures. One day after implantation of tumor cells, graded doses of FR-900216 substance were administered to mice intraperitoneally. The samples of FR-900216 substance used in the experiment were solubilized in methanol, concentrated in vacuo and then suspended in the sterilized water. Treatment is Q4D on days 1, 5 and 9. Control mice received intraperitoneal doses of physiological saline solution. The injection volume was 0.2 ml in all experiments. Six mice were used for each experimental group. At day 1 and day 11, tumor length and tumor width were measured. The antitumor activity was calculated according to the protocols for selected in vivo models in NCI, USA.

Result

The result is shown in Table 4.

TABLE 4

| Dosed/Control | Dose (mcg/kg) | T/C × 100 |
|---|---|---|
| dosed with FR-900216 substance | 2000 | −26 |
| | 1000 | 3 |
| | 500 | 2 |
| | 250 | 34 |
| Control | — | 100 |

The following Preparations are given for the purpose of illustrating the preparation of FR-900216 substance.

Preparation 1

Seed medium (80 ml) containing corn starch (1%), glucose (0.5%), gluten meal (1%), dried yeast (1%) and corn steep liquor (1%) (adjusted to pH 7.0 before sterilization) was poured into each of six 275 ml-Erlenmeyer flasks and sterilized at 120° C. for 30 minutes. A loopful of slant culture of Rhizopus sp. No. F-1360 ATCC 20577 was inoculated to each of the media and cultured at 30° C. for 48 hours at 250 rpm using a rotary shaker. The total volume of thus obtained seed culture was inoculated again to a seed medium (20 liters) containing a soluble starch (2%), glycerin (0.5%), glucose (0.5%), gluten meal (1%), dried yeast (1%), corn steep liquor (1%) (adjusted to pH 7.0 before sterilization) in a 30 liter stainless jar fermentor which had been sterilized at 120° C. for 30 minutes and cultured at 30° C. for 24 hours under aeration of 1 VVM and agitation of 200rpm. Further, total volume of thus obtained seed culture were inoculated to a production medium (150 liter) containing soluble starch (2%), glycerin (0.5%), dried yeast (1%), cottonseed flour (1%) soy been meal (0.5%) and calcium carbonate (%) (pH 7.0) in a 200-liter stainless jar fermentor which had been sterilized at 120° C. for 30 minutes and cultured at 30° C. for 72 hours under aeration of 0.7 VVM and agitation of 250 rpm.

The cultured broth thus obtained was filtered with an aid of diatomaseous earth (5 kg). To the mycelia obtained were added 80 liters of ethyl acetate and extracted. This extraction procedure was carried out twice and the extracts were combined. The extract was concentrated in vacuo to a volume of 1 liter. The concentrate was washed with aqueous sodium bicarbonate solution (0.5%, 500 ml), dried over anhydrous sodium sulfate and further concentrated in vacuo to a volume of 300 ml. The concentrate thus obtained was applied to a column chromatography using silica gel (2500 ml). The column was washed with chloroform, and then eluted with a mixture of chloroform and methanol (100:1). Fractions containing FR-900216 substance were concentrated to a volume of 20 ml. To the concentrate hexane (1.5 liter) was added and filtered. Thus obtained precipitate was dried to give a crude powder (1.1 g). The crude powder was dissolved in methanol (100 ml) and then was applied to a reverse phase column chromatography using NS Gel (1500 ml, made by Nihon Seimitsukagaku Co., Ltd.). The column was eluted with methanol and fractions containing FR-900216 substance were collected (total 800 ml) and were concentrated to a volume of 10 ml. Hexane (1 liter) was added to the concentrate and filtered. Thus obtained precipitate was dried to give a power (630 mg). The powder was purified using thin-layer chromatography (developing solvent: chloroform : methanol=20:1). Bands containing FR-900216 substance were collected and suspended in a mixture of chloroform and methanol (10:1). The extract was concentrated to a volume of 5 ml and added to hexane (500 ml) to give a colorless powder of FR-900216 substance (300 mg).

Elemental Analysis: C: 66.30(%), H: 7.61(%), N: 2.18(%).

Preparation 2

Seed medium (80 ml) containing corn starch (1%), glucose (0.5%), gluten meal (1%), dried yeast (1%) and corn steep liquor (1%) (adjusted to pH 7.0 before sterilization) was poured into each of six 275 ml-Erlenmeyer flasks and sterilized at 120° C. for 30 minutes. A loopful of slant culture of Rhizopus sp. No. F-1360 ATCC 20577 was inoculated to each of the media and cultured at 30° C. for 48 hours at 250 rpm using a rotary shaker. The total volume of thus obtained seed culture was inoculated again to a seed medium (20 liters) containing a soluble starch (2%), glycerin (0.5%), glucose (0.5%), gluten meal (1%), dried yeast (1%), corn steep liquor (1%) (adjusted to pH 7.0 before sterilization) in a 30 liter stainless jar fermentor which had been sterilized at 120° C. for 30 minutes and cultured at 30° C. for 24 hours under aeration of 1 VVM and agitation of 200 rpm. Further, total volume of thus obtained seed culture were inoculated to a production medium (150 liter) containing soluble starch (2%), glycerin (0.5%), dried yeast (1%), cottonseed flour (1%) soy been meal (0.5%) and calcium carbonate (pH 7.0) in a 200 liter stainless jar fermentor which had been sterilized at 120° C. for 30 minutes and cultured at 30° C. for 72 hours under aeration of 0.7 VMM and agitation of 250 rpm.

The cultured broth thus obtained was filtered with an aid of diatomaseous earth (5 kg). To the mycelia obtained were added 80 liters of ethyl acetate and extracted. This extraction procedure was carried out twice and the extracts were combined. The extract was concentrated in vacuo to a volume of 1 liter. The concentrate was washed with aqueous sodium bicarbonate solution (0.5%, 500 ml), dried over anhydrous sodium sulfate and further concentrated in vacuo to a volume of 300 ml. The concentrate thus obtained was applied to a column chromatography using silica gel (2500 ml). The column was washed with chloroform, and then eluted with a mixture of chloroform and methanol (100:1). Fractions containing FR-900216 substance were concentrated to a volume of 50 ml. To the concentrate hexane (2 liter) was added and filtered. Thus obtained precipitate was dried to give a crude powder (2.5 g). The crude powder was dissolved in 10 ml of chloroform and subjected to high performance liquid chromatography (made by Nippon Water Limited Co., Ltd., column: Prepack 500 packed with silica gel) and eluted with a mixture of chloroform and methanol (100 : 15). Thus obtained fractions containing FR-900216 substance were collected, concentrated in vacuo to a volume of 10 ml and added to hexane (100 ml) to give a precipitate. Thus obtained precipitate was dried to give a power (1.2 g). This procedure was conducted once more to give a colorless powder of FR-900216 substance (500 mg).

The following examples were given for the purpose of illustrating the present invention.

EXAMPLE 1

Suspension for intramascular infection:

| FR-900216 substance | 50 mg |
|---|---|
| polysolvate 80 | 10 mg |
| sodium chloride | 0.09 g |
| distilled water | 4 ml |

EXAMPLE 2

Emulsion for intravenous injection:

| FR-900216 substance | 5 mg |
|---|---|
| Sesame oil | 100 mg |
| polysolvate 80 | 10 mg |
| sodium chloride | 0.09 g |

EXAMPLE 3

Suspension for long acting intramuscular injection:

| FR-900216 substance | 50 mg |
|---|---|
| Sesame oil | 4 ml |

EXAMPLE 4

Tablet for oral administration:

| FR-900216 substance | 250 mg |
|---|---|
| calcium carboxymethylcellulose | 35 mg |
| hydroxypropylcellulose | 4 mg |
| magnesium stearate | 7 mg |
| lactose | 84 mg |
| (total weight: 370 mg) | |

What we claim is:

1. A pharmaceutical composition for treating lymphocytic leukemia, melanoma or mammary carcinoma comprising an effective amount of FR-900216 substance having the following physical and chemical properties:
(1) Molecular weight:
625 (Mass spectrum)
(2) Molecular formula:
$C_{35}H_{47}NO_9$
(3) Melting point:
130°–135° C. (dec.)
(4) Specific rotation:
$[\alpha]_D^{20} = +140°$ C. (c=1, CHCl$_3$)
(5) Ultraviolet absorption spectrum:

$\lambda_{max}^{CH3OH} = 232$ nm ($\epsilon = 11,300$)

$= 238$ nm (sh.)

$= 285$ nm (sh.)

$= 296$ nm ($\epsilon = 55500$)

$= 308$ nm ($\epsilon = 70300$)

$= 324$ nm ($\epsilon = 51900$)

(6) Infrared absorption spectrum:
$\nu_{max}^{KBr}$: 3450, 3140, 2960, 2920, 1730, 1715 (sh.), 1607, 1575, 1455, 1445, 1435, 1377, 1360, 1343, 1305, 1280, 1260, 1225, 1190, 1170, 1140, 1107, 1077, 1045, 1030 (sh.), 980, 970, 950, 930, 915, 905, 895, 875, 860, 850, 835, 825, 790, 780, 755, 705, 670, 635 cm$^{-1}$
(7) $^1$H Nuclear magnetic resonance spectrum (CDCl$_3$, inner standard: tetramethylsilane):
as shown in FIGURE of the accompanying drawing,
(8) $^{13}$C Nuclear magnetic resonance spectrum (CDCl$_3$, inner standard: tetramethylsilane):
δ (ppm): 9.65, 11.41, 11.71, 13.77, 14.32, 16.93, 22.57, 29.24, 31.49, 31.85, 34.16, 35.86, 36.40, 37.98, 45.32, 54.18, 56.12, 63.77, 65.10, 76.81, 82.33, 89.25, 120.80, 123.77, 126.44, 129.29, 135.97, 136.21, 136.57, 137.67, 138.51, 139.54, 160.84, 168.01, 169.34
(9) Solubility:
Freely soluble: methanol, ethanol, acetone, ethyl acetate
Soluble: chloroform, benzene
Slightly soluble: hexane, diethyl ether
Insoluble: water
(10) Color reaction:
Positive: Dragendorff's reaction, iodine reaction
Negative: Ferric chloride reaction, Molisch's reaction, Ninhydrin reaction, Ehrlich's reaction
(11) Nature:

Weakly basic substance or pharmaceutically acceptable salt thereof in association with a pharmaceutically acceptable, substantially non-toxic carrier or excipient.

2. A method of treating lymphocytic leukemia, melanoma or mammary carcinoma in a subject in need of such treatment comprising administering to said subject an effective amount of a pharmaceutical composition comprising an effective amount of FR-900216 substance having the following physical and chemical properties:
(1) Molecular weight:
625 (Mass spectrum)
(2) Molecular formula:
$C_{35}H_{47}NO_9$
(3) Melting point:
130°–135° C. (dec.)
(4) Specific rotation:
$[\alpha]_D^{20} = +140°$ C. (c=1, CHCl$_3$)
(5) Ultraviolet absorption spectrum:

$\lambda_{max}^{CH_3OH} = 232$ nm ($\epsilon = 11,300$)

$= 238$ nm (sh.)

$= 285$ nm (sh.)

$= 296$ nm ($\epsilon = 55500$)

$= 308$ nm ($\epsilon = 70300$)

$= 324$ nm ($\epsilon = 51900$)

(6) Infrared absorption spectrum:
$\nu_{max}^{KBr}$: 3450, 3140, 2960, 2920, 1730, 1715 (sh.), 1607, 1575, 1455, 1445, 1435, 1377, 1360, 1343, 1305, 1280 (sh.), 980, 970, 950, 930, 915, 905, 895, 875, 860, 850, 835, 825, 790, 780, 755, 705, 670, 635, cm$^{-1}$ (7) $^1$H Nuclear magnetic resonance spectrum (CDCl$_3$, inner standard: tetramethylsilane):
as shown in FIGURE of the accompanying drawing, (8) $^{13}$C Nuclear magnetic resonance spectrum (CDCl$_3$, inner standard: tetramethylsilane):
$\delta$ (ppm): 9.65, 11.41, 11.71, 13.77, 14.32, 19.93, 22.57, 29.24, 31.49, 31.85, 34.16, 35.86, 36.40, 37.98, 45.32, 54.18, 56.12, 63.77, 65.10, 76.81, 82.33, 89.25, 120.80, 123.77, 126.44, 129.29, 135.97, 136.21, 136.57, 137.67, 138.51, 139.54, 160.84, 168.01, 169.34

(9) Solubility:
Freely soluble: methanol, ethanol, acetone, ethyl acetate
Soluble: chloroform, benzene
Slightly soluble: hexane, diethyl ether
Insoluble: water

(10) Color reaction:
Positive: Dragendorff's reaction, iodine reaction
Negative: Ferric chloride reaction, Molisch's reaction, Ninhydrin reaction, Ehrlich's reaction

(11) Nature:
Weakly basic substance or pharmaceutically acceptable salt thereof in association with a pharmaceutically acceptable, substantially non-toxic carrier or excipient.

* * * * *